(12) United States Patent
Manzoli

(10) Patent No.: US 6,302,691 B1
(45) Date of Patent: Oct. 16, 2001

(54) USE INDICATING MEANS FOR DENTAL FILES

(76) Inventor: Nicholas J. Manzoli, 56 Whisper Dr., Worcester, MA (US) 01609

(*) Notice: Subject to any disclaimer, the term of this patent is extended or adjusted under 35 U.S.C. 154(b) by 0 days.

(21) Appl. No.: 09/667,664

(22) Filed: Sep. 22, 2000

Related U.S. Application Data

(60) Provisional application No. 60/155,838, filed on Sep. 24, 1999.

(51) Int. Cl.$^7$ .................................................. A61C 19/04
(52) U.S. Cl. .............................................. 433/72; 433/102
(58) Field of Search ............................. 433/72, 75, 102, 433/224

(56) References Cited

U.S. PATENT DOCUMENTS

| | | |
|---|---|---|
| 3,568,627 | 3/1971 | Silinger et al. . |
| 3,704,096 | 11/1972 | Verses et al. . |
| 4,044,468 | 5/1977 | Kahn . |
| 4,340,364 | 7/1982 | Deemer . |
| 4,734,035 * | 3/1988 | Cheng et al. ................ 433/102 |
| 4,836,780 | 6/1989 | Buchanan . |
| 5,154,611 * | 10/1992 | Chen .............................. 433/72 |
| 5,380,200 | 1/1995 | Heath et al. . |
| 5,476,792 | 12/1995 | Ezrielev et al. . |
| 5,723,336 | 3/1998 | Barrett . |
| 5,752,825 | 5/1998 | Buchanan . |
| 5,839,986 | 11/1998 | Hickok et al. . |
| 5,879,160 | 3/1999 | Ruddle . |

* cited by examiner

Primary Examiner—Nicholas D. Lucchesi
(74) Attorney, Agent, or Firm—Blodgett & Blodgett, P.C.

(57) ABSTRACT

In general, the invention consists of an indicator means for indicating the usage of an endodontic instrument by providing a visual indication of the number of sterilizations of the instrument. The indicator includes a modified "stop" or "washer" which is used with each endodontic instrument. The "stop" includes a dye compatible base which is impregnated with a diffusible dye composition. The base is made of a dye compatible material which enables the diffusible dye to migrate or diffuse as a result of a specific number of sterilizations at a specific temperature from an interior portion in the base where the dye is not visible to an exterior position where the dye is visible. Since the "stop" is also sterilized along with the instrument, the "stop" will change color after a specified number of sterilizations of the instrument has occurred. Since each endodontic instrument is sterilized after each use, the change in color of the "stop" will also provide a visual indicator of the number of times the endodontic instrument has been used. More specifically, the base is of pure polymer composition, essentially free of additives, and the dye is any of various known polymer compatible dyes capable of diffusing within a dye compatible polymer. An alternate configuration of the invention utilizes materials of different melting points instead of diffusible dyes in the wells on the instrument handles.

22 Claims, 4 Drawing Sheets

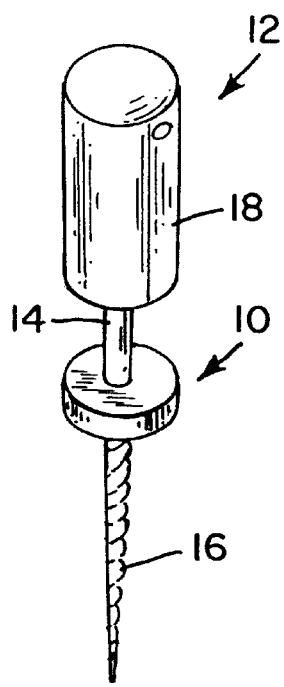
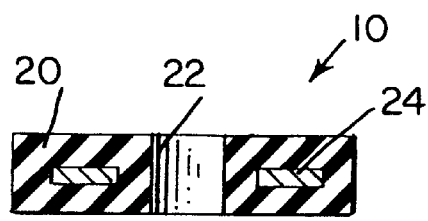
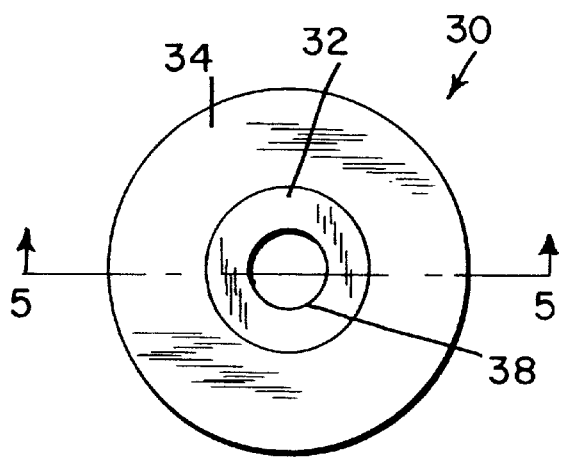
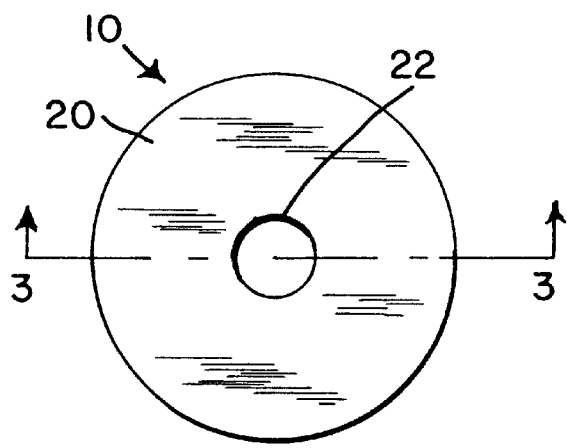
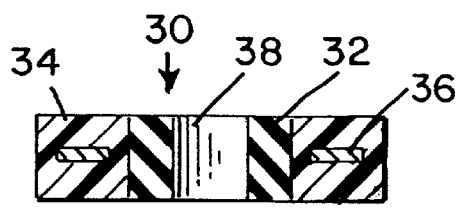

USE INDICATING MEANS FOR DENTAL FILES

CROSS-REFERENCE TO RELATED APPLICATIONS

This application claims the benefit under 35 U.S.C. §119 (e) of prior U.S. Provisional application Ser. No. 60/155,838 filed Sep. 24, 1999; which is hereby incorporated by reference.

STATEMENT REGARDING FEDERALLY SPONSORED RESEARCH OR DEVELOPMENT

This invention has been created without the sponsorship or funding of any federally sponsored research or development program.

BACKGROUND OF THE INVENTION

The present invention is directed generally to a time-temperature indicator device for indicating a specified number of time-temperature events such as sterilizations of a medical instrument. The invention is directed, more specifically, to a device for indicating a specified number of uses and subsequent sterilizations of files for use in endodontic operations, i.e. root canal therapy.

In many endodontic operations, it is necessary to successively insert an elongated instrument into, and then pull the same from the root canal of a tooth in order to thoroughly remove any inflamed or necrotic tissue therein and properly enlarge the canal. The instrumented root canal is subsequently sealed off with aseptic material.

The conventional endodontic instrument which is used in the root canal treatment described above, generally consists of a thin flexible wire with an abrasive surface acting as a file, a reamer, or the like, a handle, and a stop of elastomeric material such as natural or synthetic rubber. The handle, which is adapted for gripping by the operator, is securely fixed at one end of the wire. The rubber stop, on the other hand, is movably attached to the wire and can be easily relocated therealong.

It is generally known that a human tooth consists of pulp chamber, root canal, enamel, dentin, and cementum, wherein the pulp chamber and the root canal are composed of nerve tissue and blood vessels. Therefor, when the tissue of the pulp suffers from traumatic injury, caries and periodontal infection, inflammation or necrosis of the pulp tissue will occur. Endodontic therapy, generally called "root canal treatment" is necessary to retain the tooth. The main work required for the endodontic therapy is to thoroughly remove the inflamed or necrotic pulp tissue, and then to seal up the root canal with aseptic material. In order to successfully perform the endodontic therapy, the root canal length of the involved tooth must be exactly measured before the root canal is sealed up. Accordingly, the most important work in endodontic therapy is to measure the exact root canal length of the tooth because only when debridement is performed completely in the tooth can the root canal be sealed up thereat.

Concerning the measurement of the root canal length, various methods are adopted in endodontic therapy, and one of the frequently used methods is X-ray, for which a reamer, or file, is inserted into the root canal, and then an endodontic stop, movably attached to the reamer or file, is adjusted to have its bottom surface kept in contact with the incisal edge, or the cusp tip of the tooth for being X-rayed thereat. The position of the stop at the wire determines the working length of the instrument, i.e., the length of the wire to be embedded in the tooth during the treatment, since the stop prevents further penetration of the wire into the canal in the tooth when its bottom surface bumps onto the incisal edge or cusp tip of the tooth being treated.

Historically, endodontic files and reamers have been composed of differing shapes of sinless steel wire that has been ground, or more often twisted to provide a cutting edge. More recently, nickel-titanium compounds have been used to construct these files to improve their properties and efficiencies. While much has been made of the improvement of these files, one of their biggest drawbacks is the increased incidence of breakage while in the root canal. This is not a desirable outcome, and can have serious medical and legal ramifications in that it may be the direct result of the failure of the root canal therapy being performed. Dentists and file manufacturers should want to decrease the incidence of file breakage in the canal by whatever means possible. Devices have been invented to remove obstructions such as broken instruments from root canals. However, it is always preferable to prevent the obstruction in the first place.

Statistically, the incidence of fracture of the nickel-titanium, as well as other endodontic file breakage increases with additional uses, and with repeated sterilization. No automatic method of monitoring usage or sterilization of these instruments currently exists.

These and other difficulties experienced with the use of endodontic instruments and attempts to monitor usage of the instruments have been obviated by the present invention.

It is, therefore, a principle object of the invention to provide a mechanism for monitoring usage and subsequent sterilization of endodontic instruments.

A further object of the invention is the provision of a mechanism for providing a visual indication of usage and sterilization of endodontic instruments which is relatively simple to make and easy to use.

Another object of the invention is the provision of a dental file having time-temperature indicator means of the handle of the file.

BRIEF SUMMARY OF THE INVENTION

In general, the invention consists of indicator means for indicating the usage of an endodontic instrument by providing a visual indication of the number of sterilizations of the instrument. The indicator means includes a modified "stop" or "washer" which is used with each endodontic instrument. The "stop" includes a dye compatible base which is impregnated with a diffusible dye composition. The base is made of a dye compatible material which enables the diffusible dye to migrate from the dye composition and diffuse through the dye compatible material as a result of a specific number of sterilizations at a specific temperature from an interior portion in the base where the dye is not visible to an exterior position where the dye is visible. Since the "stop" is also sterilized along with the instrument, the "stop" will change color after a specified number of sterilizations of the instrument has occurred. Since each endodontic instrument is sterilized after each use, the change in color of the "stop" will also provide a visual indicator of the number of times the endodontic instrument has been used. More specifically, the base is of pure polymer composition, essentially free of additives, and the dye is any of various known polymer compatible dyes capable of diffusing within a dye compatible polymer. The indicator section has a first part of a dye compatible material and a second part of a dye composition in contact with the first part so that dye from the second part diffuses through the second part as a result of heating sterilization of the dental file to indicate a predetermined number of sterilizations of the dental files. Each indicator section requires a different amount of time at a predetermined temperature for the dye to diffuse through the first part of the indicator section.

An alternate configuration of the invention utilizes materials of different melting or sublimation points instead of diffusible dyes in the wells on the instrument handles.

BRIEF DESCRIPTION OF THE DRAWINGS

FIG. 1 is an isometric view of an endodontic file equipped with a stop embodying the principles of the present invention;

FIG. 2 is a plan view of the stop;

FIG. 3 is a vertical cross-sectional view of the stop, taken along line III—III of FIG. 2 and looking in the direction of the arrows;

FIG. 4 is a plan view of a first modified stop embodying the principles of the prevent invention;

FIG. 5 is a vertical cross-sectional view of the stop of FIG. 4 taken along line 5—5 of FIG. 4 looking in the direction of the arrows;

DETAILED DESCRIPTION OF THE INVENTION

Figure 6:
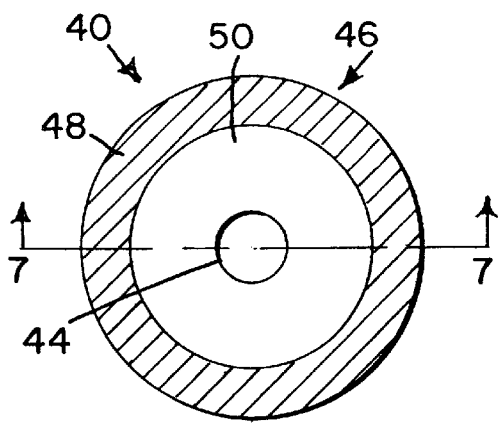
FIG. 6 is a plan view of a second modified stop embodying the principles of the present invention.

Referring first to FIG. 1, there is shown a stop for an endodontic file embodying the principles of the present invention. The stop is generally indicated by the reference numeral 10 and is shown in FIG. I as applied to the shank portion 14 of an endodontic file generally indicated by the reference numeral 12. The file 12 has a handle 18 fixed to one end of the shank 14 and an abrasive surface 16 at the opposite end of the shank 14. The stop 10 is located between the handle 18 and the abrasive surface 16.

Referring to FIGS. 2 and 3, the stop 10 comprises a disc 20 of a dye compatible elastomeric material such as silicon rubber which has a central aperture 22. A ring-shaped dye composition 24 is embedded within the disc 20. The dye composition 24 is compatible with the elastomeric material of the disc 20 so that when the disc 20 is heated to a predetermined temperature, the dye from the composition 24 migrates through the disc 20. The material of disc 20 is colorless so that when the file 12 within the stop 10 applied thereto is sterilized for a specific length of time at a specific temperature, the dye from the dye composition 24 will migrate to the outer surfaces of the disc 20 to serve as a visual indicator that a specific number of sterilization events have occurred. This serves as an indication that the file and stop have been used in an endodontic procedure for a specified number of times.

Referring to FIGS. 4 and 5, there is shown a first modified stop, generally indicated by the reference numeral 30, which comprises an outer ring 34 and an inner ring 32. The outer ring 34 is a dye compatible polymer which contains a polymer compatible dye composition 36 within the outer ring 34. The inner ring 32 is made of an elastomeric material, such as natural or synthetic rubber, and contains a central aperture 38. The outer ring 34 is colorless so that when the stop 30 is heated to a predetermined temperature for a predetermined length of time, the dye from the composition 36 migrates to the outer surfaces of the ring 34 so that the dye is visible by the user and serves as a visual indication that the stop 30 has undergone a predetermined number of sterilization events and that the file and stop have been used in an endodontic procedure for a specified number of times.

Figure 7:
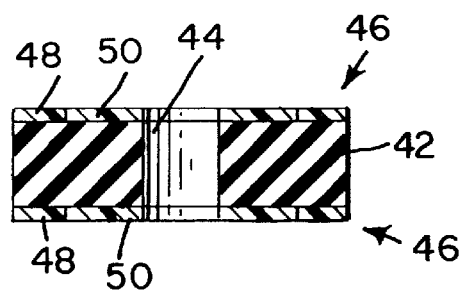
FIG. 7 is a vertical cross-sectional view of the stop of FIG. 6 taken along the line 7—7 of FIG. 6.
Figure 8:
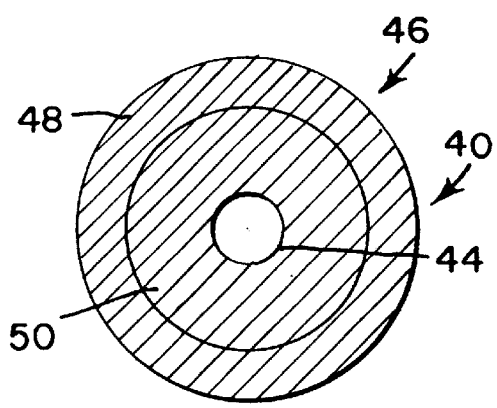
FIG. 8 is a plan view of the stop of FIG. 6 showing the stop after it has been subjected to a specified number of dent sterilizations.

Referring to FIGS. 6–8, a second modified stop is generally indicated by the reference numeral 40 and comprises a disc 42 of elastomeric material which has a central aperture 44. A dye compatible polymer film, generally indicated by the reference numeral 46, is fixed to each broad surface of the disc 42, i.e., by adhesive. The polymer film 46 has a clear, or colorless inner area 50 and a dye containing outer area 48 which is shown in FIG. 6 as an outer ring-shaped portion of the film 46. When the stop 40 has been heated to a predetermined temperature for a predetermined length of time, dye from the outer area 48 migrates through the polymer film 46 into the inner area 50 so that the entire film assumes the color of the dye as shown in FIG. 8 to serve as a visual indication that a specific number of sterilization events have occurred. Many types of dye compositions and dye compatible polymer compositions are known, many of which are described in U.S. Patent of Ezrielev et al., U.S. Pat. No. 5,476,792. The disclosure of this patent is incorporated herein by reference.

Figure 9:
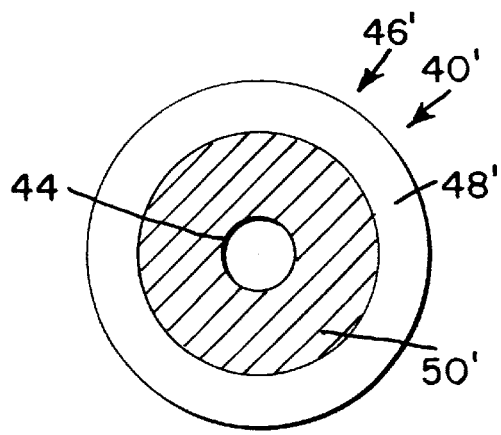
FIG. 9 is a plan view of a variant of the second modified stop of FIG. 6.
Figure 10:
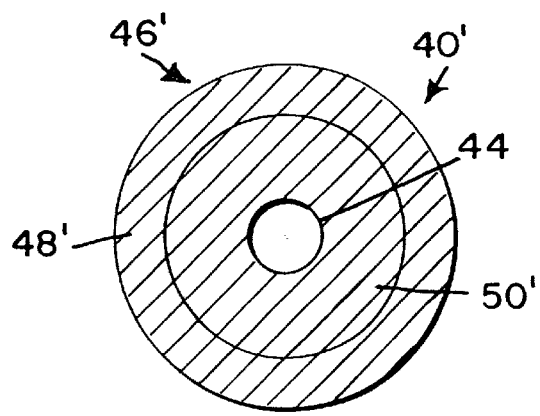
FIG. 10 is a plan view of the stop of FIG. 9 after it has been subjected to a specified number of heat sterilizations.

FIG. 9 is a plan view of a variant of the modified stop of FIG. 6 which is generally indicated by the reference numeral 40'. Stop 40' has a dye compatible polymer film, generally indicated by the reference numeral 46', which is fixed to both broad sides of the disc 42. The film 46' has an inner dye containing area 50' which surrounds the aperture 44 and an outer clear or colorless ring-shaped area 48' which surrounds the inner area 50'. When the stop 40' has been heated to a predetermined temperature for a predetermined length of time, dye from the inner area 50' migrates through the polymer film 46' into the outer area 48' so that the entire film assumes the color of the dye as shown in FIG. 10 to serve as a visual indication that a specific number of sterilization events have occurred.

Referring to FIGS. 11–15 there is shown a first modified dental file, generally indicated by the reference numeral 60. File 60 has a handle portion 62 and a shank portion 64.

The handle portion 62 of the file 60 has applied thereto spaced indicator sections, generally indicated by reference numerals 66, 67, 68 and 69. Each of the indicator sections has a first part 73 of a layer of dye compatible polymer composition and a second part 72 of a dye composition which is in contact with the polymer composition of the first part 73. Each first part 73 is circular. Each second part 72 is ring-shaped and is super-imposed on the first part 73 at the peripheral edge of the first part so that most of the first part is surrounded by the second part. The first part 73 of the indicator sections 66, 67, 68 and 69 have the same area. The second part 72 of the indicator sections 66, 67, 68 and 69 have the same area. However, the polymer composition of the first part of each of the indicator sections 66, 67, 68 and 69 has a different time temperature diffusion rate for the dye in the second part 72.

Figure 11:
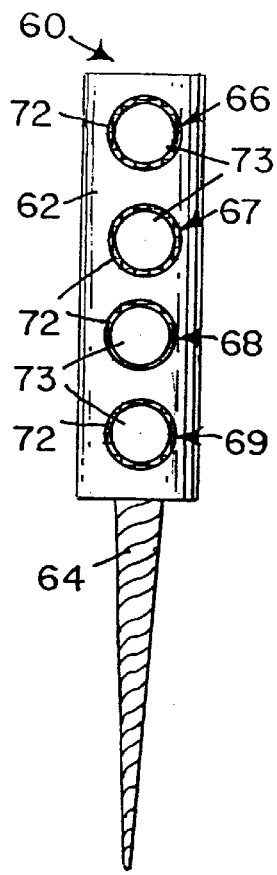
FIGS. 11–15 are side elevational sequential views of a first modified dental file in which the handle portion of the file is provided with a first time temperature indicator means.

FIG. 11 shows the status of the file 60 prior to any sterilization events in which the area within each ring of dye composition 72 is clear.

Figure 12:
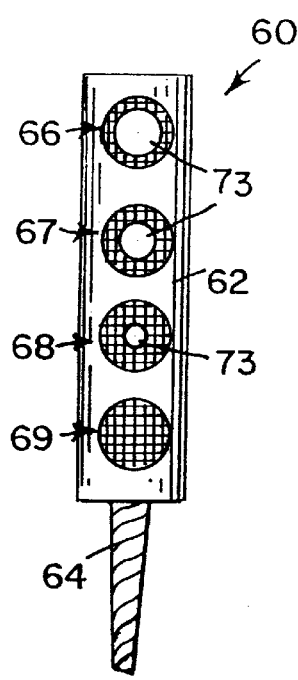

FIG. 12 shows the status of the file 60 after a predetermined of sterilizations has occurred, i.e., one sterilization. Diffusion of the dye from the dye composition 72 has occurred in the polymer compositions of each of the first parts 73 to different degrees. Total diffusion has occurred in the polymer composition of visual indicator section 69 and to a progressively lesser degree in the polymer compositions of visual indicator sections 68, 67 and 66.

Figure 13:
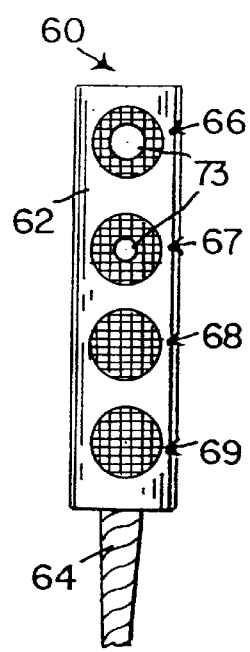

FIG. 13 shows the status of the file 60 after additional sterilizations i.e., two total sterilizations. In this case the dye has diffused completely in the polymer compositions of visual indicator sections 68 and 69.

The polymer composition for the first part of each indicator section 66, 67, 68 and 69 may be in the form of a film or coating with a printed ring pattern of the dye composition which is adhered to the outer surface of the handle portion 62. The outer surface of the handle 62 can also have a plurality of circular depressions of wells which are filled with the polymer compositions and coated with the dye compositions.

Figure 14:
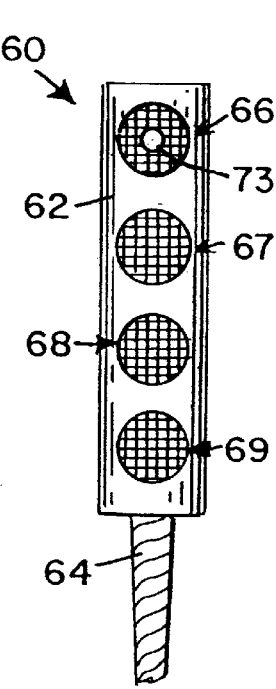

In FIG. 14 the die has completely diffused in the polymer compositions of indicator sections 69, 68, and 67, indicating a higher number of sterilizations, i.e., three sterilizations.

Figure 15:
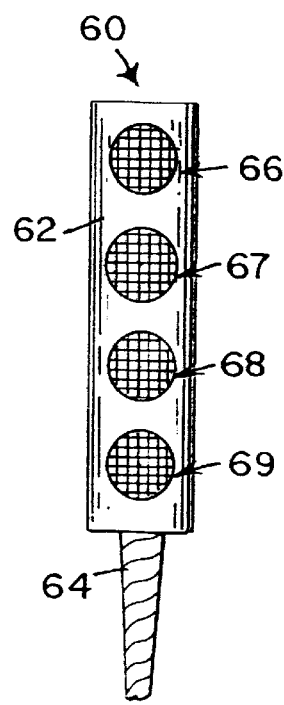

In FIG. 15 the dye has completely diffused in the polymer compositions of all indicator sections, indicating a predetermined maximum number of sterilizations, i.e., four sterilizations.

Referring to FIGS. 16–20, there is illustrated a second modified dental file, generally indicated by the reference numeral 74. File 74 has a handle portion 76 and a shank portion 78. The outer surface of the handle portion 76 is provided with a plurality of spaced circular indicator sections generally indicated by the reference numerals 80, 81, 82 and 83. Each indicator section has a first part of a dye compatible polymer composition 84.

Ring-shaped second parts 86, 88, 90 and 92 of a dye composition are superimposed on the first part of indicator sections 80, 81, 82 and 83. The polymer composition for the first part of each of the indicator sections 80, 81, 82 and 83 has the same diffusion rate for the dye in the dye compositions of the second parts 86, 88, 90 and 92. The areas of the first part of indicator sections 80, 81, 82 and 83 diminish in size from the largest circle of indicator section 80 to the smallest circle of indicator section 83. The sizes of the ring-shaped second parts 86, 88, 90 and 92 of the dye composition vary proportionally to the areas of their respective first parts of polymer composition. Dye from the second parts 86, 88, 90 and 92 diffuse into the first parts of indicator sections 80, 81, 82 and 83 at the same rate in accordance with the time-temperature diffusion rating of the polymer composition of the first parts. However, the rate at which the circular area of the indicator sections 80, 81, 82 and 83 is filled in with dye varies in accordance with its relative size.

Figure 16:
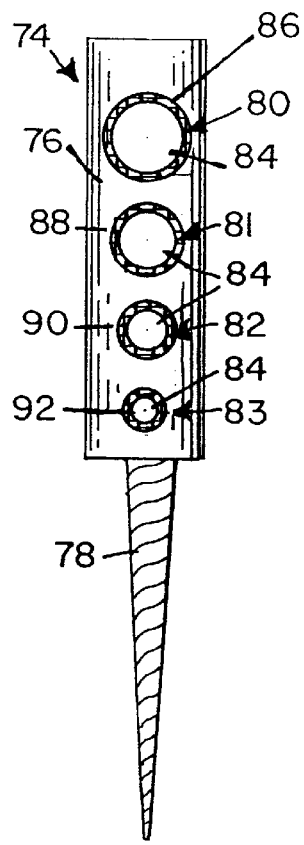
FIGS. 16–20 are side elevational sequential views of a second modified dental file in which the hand portion of the file is provided with a second time-temperature indicator means.
Figure 17:
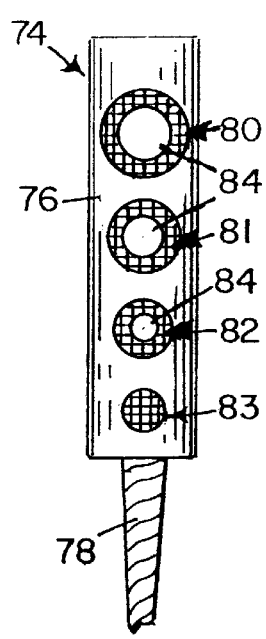
Figure 18:
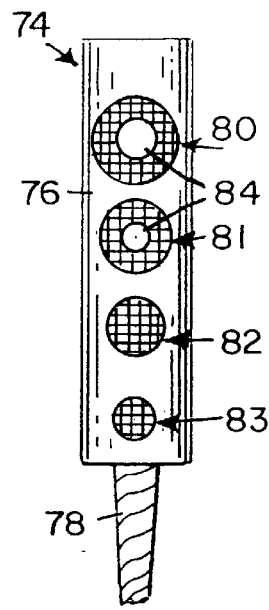
Figure 19:
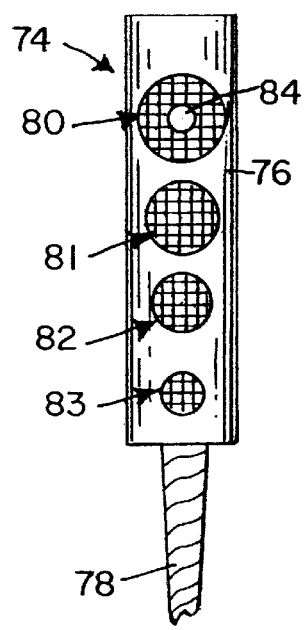
Figure 20:
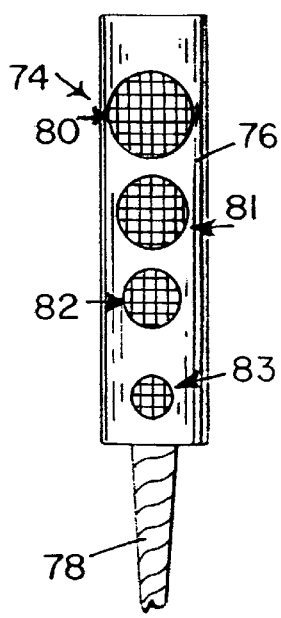

Referring specifically to FIG. 16, the dental file 74 is shown as it appears prior to any sterilization events. As shown in FIG. 16, each of the first part of indicator sections 80. 81, 82 and 83 is free of dye. The areas of the first part 84 of indicator sections 83, 82, 81 and 80 are progressively filled in with dye in the above order after a predetermined number of progressive sterilization events, i.e. one, two, three and four events, respectively. FIG. 20 shows the first parts 84 of indicator section 80, 81, 82, 83 filled in with dye, indicating that the maximum number of sterilization events has occurred. The areas of polymer composition may be in the form of a film or coating with printed rings of dye composition which is adhered to the outer surface of the handle portion 76. The outer surface of the handle portion 76 can also have circular depressions or wells which are filled with the polymer composition coated with the dye composition.

An alternate configuration of the invention utilizes materials of different dissipation (melting or sublimation) points instead of diffusible dyes in the wells on the instrument handles. The indicator sections 66–69 such as those in FIG. 15 would be indentations, or wells, in the file handle, 62, that would hold materials of specific melting or sublimation points (the sterilization temperature), or different amounts of materials of the same melting or sublimation point. The wells would be of different depths, capable of holding different amounts of material. Upon each sterilization cycle, material would dissipate (melt or sublimate) out of each well. An indicator at the base of each well would become visible when it was completely empty. The different depths of each well would cause the indicator to be displayed after fewer cycles in the shallower wells, and after more cycles in the deeper wells, thus indicating the number of sterilizations, or times the instrument has been utilized.

Minor changes may be made in the form and construction of the invention without departing from the materials spirit, thereof. It is not, however, desired to confine the invention to the exact form herein shown and described, but is desired to include all such as properly come within the scope claimed.

The invention having been thus described, what is claimed as new and desired to secure by letters patent is:

What is claimed:

1. A use indicator for a dental file, said use indicator comprising:
   (a) a body adapted for application to said dental file, said body having an outer surface and a first portion which includes at least a portion of said outer surface and is made of a material which enables a dye which is compatible with said material to diffuse through said material when said body is heated to a predetermined temperature, said body having a second portion in contact with said first portion; and
   (b) a quantity of said dye in said second portion so that said dye is capable of migrating from said second portion to said first portion and diffusing through said first portion when said body is heated to a predetermined temperature for a predetermined period of time for indicating a predetermined number of heating sterilizations of the instrument to which said use indicator is applied.

2. The use indicator as recited in claim 1, wherein said second portion is an interior portion of said body spaced from said outer surface.

3. The use indicator as recited in claim 1, wherein said body, including said first portion, is made of an elastomeric material.

4. The use indicator as recited in claim 1, wherein said file has a cylindrical shank portion and said body is disc-shaped stop with a central cylindrical aperture for receiving said file for enabling said body to be positioned on said shank portion.

5. The use indicator as recited in claim 4, wherein said body is made of an elastomeric material.

6. The use indicator as recited in claim 4, wherein a portion of said body surrounding said aperture is an elastomeric material and the remainder of said body is a non-elastomeric polymer.

7. The use indicator as recited in claim 4, wherein body comprises:

(a) a main inner core portion of elastomeric material; and (b) an outer planar portion which includes said first portion and said second portion.

8. The use indicator as recited in claim 7, wherein one of said first portion and said second portion is ring-shaped and surrounds said aperture, and the other of said first portion and said second portion is ring-shaped and surrounds said one of said first portion and said second portion.

9. The use indicator as recited in claim 8, wherein said first portion surrounds said aperture and said second portion surrounds said first portion.

10. The use indicator as recited in claim 8, wherein said second portion surrounds said aperture and said first portion surrounds said second portion.

11. The use indicator as recited in claim 7, wherein said aperture has a central longitudinal axis and said inner core portion has a flat surface within a plane which is transverse to said longitudinal axis and said first and second portions are in a polymer film fixed to said flat surface.

12. The use indicator as recited in claim 7, wherein said first portion is colorless.

13. The use indicator as recited in claim 1, wherein said first portion is colorless.

14. A dental file comprising:

(a) a shank portion having an outer abrasive surface; and (b) a handle portion connected to the shank portion, said handle portion having an outer surface which has a plurality of spaced indicator sections, each of said indicator sections having a first part of a material which enables a dye which is compatible with said material to migrate through said material when said dental file is heated to a predetermined temperature, each of said indicator sections having a second part in contact with said first part and containing a quantity of said dye so that said dye is capable of migrating from said first part into said second part and diffusing through said second part when said dental file is heated to said predetermined temperature for a predetermined period of time, each of said indicator sections requiring a different amount of time at said predetermined temperature for the dye in the adjacent second part of the indicator section to diffuse throughout the first part of the indicator section for indicating a predetermined number of heating sterilizations of said dental file.

15. The dental file as recited in claim 14, wherein one part of the first part and the second part of each of said indicator section is circular and the other part of the first part and the second part of each of said indicator sections is ring shaped and substantially surrounds said one part.

16. The dental file as recited in claim 15, wherein the first part of each of said indicator sections is surrounded by the second part of the indicator section.

17. The dental file as recited in claim 16, wherein the first part of each of said indicator sections has an area which differs from the area of each of the others of said locator sections so that the first part of each of said indicator sections requires a different amount of time for said dye to migrate throughout the first part.

18. The dental file as recited in claim 16, wherein each of the first parts of said indicator sections have the same area and, wherein the material in the first part of each of said indicator sections has a rate at which said dye migrates through the first part which differs from that of the others of said indicator second so that the first part of each of said indicator sections requires a different amount of time for said dye to migrate throughout the fist part.

19. The dental file as recited in claim 14, wherein the first part of each of said indicator sections has an area which differs from the area of each of the others of said indicator sections so that the first part of each of said indicator sections requires a different amount of time for said dye to migrate throughout the first part.

20. The dental file as recited in claim 14, wherein each of the firs parts of said indicator sections have the same area and, wherein the material in the first part of each of said indicator sections has a rate at which said dye migrates through the first part which differs from that of the others of said indicator section so that the first part of each of said indicator sections requires a different amount of time for said dye to migrate throughout the first part.

21. The dental file as recited in claim 14, wherein the material of the first part of each of said indicator sections is colorless.

22. A dental file comprising:

(a) a shank portion having an outer abrasive surface; and (b) a handle portion connected to the shank portion, said handle portion having an outer surface which has a plurality of spaced indicator sections, each of said indicator sections consisting of a well having a chosen depth and containing a material which dissipates when said dental file is heated to a predetermined temperature, each of said indicator sections having a base and an indicator thereon the visibility of the indicator indicating a predetermined number of heating sterilizations of said dental file.

* * * * *